(12) United States Patent
Krufka (10) Patent No.: US 9,945,774 B2
(45) Date of Patent: Apr. 17, 2018

(54) CHANNEL LIGHT MEASUREMENT APPARATUS HAVING REDUCED SIGNAL-TO-NOISE RATIO

(71) Applicant: Siemens Healthcare Diagnostics Inc., Tarrytown, NY (US)

(72) Inventor: Frank Krufka, Kirkwood, PA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 133 days.

(21) Appl. No.: 14/396,639

(22) PCT Filed: Apr. 19, 2013

(86) PCT No.: PCT/US2013/037303
§ 371 (c)(1),
(2) Date: Oct. 23, 2014

(87) PCT Pub. No.: WO2013/163017
PCT Pub. Date: Oct. 31, 2013

(65) Prior Publication Data
US 2015/0099309 A1 Apr. 9, 2015

Related U.S. Application Data

(60) Provisional application No. 61/637,712, filed on Apr. 24, 2012.

(51) Int. Cl.
*G01N 21/31* (2006.01)
*G01J 1/44* (2006.01)
(Continued)

(52) U.S. Cl.
CPC ............ *G01N 21/31* (2013.01); *G01J 1/44* (2013.01); *G01J 3/0264* (2013.01);
(Continued)

(58) Field of Classification Search
CPC ............ G01N 21/31; G01N 15/0205; G01N 15/1459; G01N 15/1463; G01N 15/0211;
(Continued)

(56) References Cited

U.S. PATENT DOCUMENTS

| 4,057,727 A | * | 11/1977 | Muehllehner | ......... A61B 6/037 |
| | | | | 250/363.03 |
| 4,948,256 A | * | 8/1990 | Lin | ......................... G01J 3/02 |
| | | | | 356/328 |

(Continued)

FOREIGN PATENT DOCUMENTS

| EP | 0 399 057 A1 | 11/1990 |
| EP | 1 049 055 A2 | 11/2000 |
| WO | 2005/091923 A2 | 10/2005 |

OTHER PUBLICATIONS

PCT International Search Report and Written Opinion dated Aug. 9, 2013 (12 Pages).

(Continued)

*Primary Examiner* — Yelena G Gakh (57) ABSTRACT

Disclosed is a multi-channel light measurement system adapted to illuminate and measure a test sample in a vessel. The multi-channel light measurement system has at least one photodetector per channel and a variable integrate and hold circuit coupled to each photodetector, the variable integrate and hold circuit allows adjustment of a sampling factor selected from a group of an integration time, a value of capacitance, an area of a discrete photodetector array, or any combination thereof. The system may readily equilibrate reference intensity output for multiple channels. Methods and apparatus are disclosed, as are other aspects.

7 Claims, 6 Drawing Sheets

(51) Int. Cl.
*G01J 3/02* (2006.01)
*G01J 3/36* (2006.01)
*G01N 21/64* (2006.01)
*G01N 21/76* (2006.01)
*G01J 3/28* (2006.01)

(52) U.S. Cl.
CPC ............... *G01J 3/2803* (2013.01); *G01J 3/36* (2013.01); *G01N 21/64* (2013.01); *G01N 21/76* (2013.01); *G01J 2003/2806* (2013.01); *G01N 2201/061* (2013.01); *G01N 2201/127* (2013.01)

(58) Field of Classification Search
CPC ..... G01N 2021/3155; G01N 2021/451; G01N 2021/8416; G01N 21/6428; G01N 21/8507; G01N 2021/6417; G01N 2021/6421; G01N 2021/6491
See application file for complete search history.

(56) References Cited

U.S. PATENT DOCUMENTS

| | | |
|---|---|---|
| 5,872,470 A | 2/1999 | Mallinson et al. |
| 5,880,459 A | 3/1999 | Pryor et al. |
| 6,331,700 B1 * | 12/2001 | Wake ................... A61B 5/0073 250/208.1 |
| 6,580,507 B2 | 6/2003 | Fry et al. |
| 7,280,204 B2 | 10/2007 | Robinson et al. |
| 7,382,408 B2 | 6/2008 | Rossi |
| 7,528,384 B2 | 5/2009 | Gratton et al. |
| 7,642,496 B2 | 1/2010 | Suzuki et al. |

OTHER PUBLICATIONS

Supplementary EP Search Report dated Nov. 30, 2015 of corresponding European Application No. 13781058.6, 5 Pages.

\* cited by examiner

CHANNEL LIGHT MEASUREMENT APPARATUS HAVING REDUCED SIGNAL-TO-NOISE RATIO

RELATED APPLICATIONS

The present application claims priority to U.S. Provisional Patent Application No. 61/637,712 filed Apr. 24, 2012, and entitled "MULTI-CHANNEL LIGHT MEASUREMENT METHODS, SYSTEMS, AND APPARATUS HAVING REDUCED SIGNAL-TO-NOISE RATIO," the disclosure of which is hereby incorporated herein by reference in its entirety for all purposes.

FIELD

The present invention relates generally to multi-channel light measurement methods, systems, and apparatus adapted to illuminate and measure one or more characteristics of a test sample.

BACKGROUND

In medical testing, photometric (light) measurement of photoluminescence, absorbance, or the like may be used as a mechanism to determine a measured characteristic of a test sample (e.g., a biological fluid). For example, in some automated testing systems (e.g., clinical analyzers) reaction vessels, such as cuvettes, flow-through vessels, sample cups, vials, and the like, may receive a biological fluid (e.g., blood, blood plasma, spinal fluid, cerebral fluid, interstitial fluid, urine, or the like), possibly containing one or more reagents or other liquids such as purified water (collectively referred to herein as a "test sample"). The test sample in the reaction vessel may be held within an illumination system. Light emissions from a light source may be projected through the test sample, and the light emanating from the test sample may be detected by one or more photodetectors. From the detected light signals, a characteristic property of interest may be determined (e.g., absorbance, luminescence, or the like) at one or more discrete emission wavelength ranges. However, existing light intensity measurement apparatus and systems may suffer from relatively high signal-to-noise ratio.

Accordingly, apparatus, systems, and methods that may improve an accuracy of such multi-channel light measurements are desired.

SUMMARY

In a method aspect, a multi-channel light measurement method is provided. The method includes receiving light emissions over a plurality of wavelength sub-ranges at an array of photodetectors wherein each photodetector in the array receives light emissions over a discrete wavelength sub-range, providing a multi-channel measurement circuit comprising multiple channels with each channel corresponding to at least one photodetector in the array of photodetectors, and adjusting a sampling factor for at least some of the channels based on a measured reference light intensity at at least some of the plurality of wavelength sub-ranges to arrive at channel reference values for at least some of the channels.

In another method aspect, a multi-channel light measurement method is provided. The method includes receiving light emissions from a light source at a plurality of photodetectors corresponding to a plurality of channels of a multi-channel light measurement system, at least some of the channels receiving different intensities from the light source over wavelength sub-ranges, adjusting sampling factors of channels of a multi-channel measurement circuit to approximately equilibrate a reference signal output for each channel and provide a reference signal value for each channel, providing a vessel containing a test sample, passing light emissions from the light source through the test sample, receiving changed light emissions at the plurality of photodetectors, wherein each photodetector in the array receives light emissions over a wavelength sub-range, passing an intensity output signal corresponding to each wavelength sub-range through the multi-channel measurement circuit to provide a measured output signal value for each channel, and determining a characteristic of the test sample based upon the measured output signal value for each channel and the reference signal value for each channel.

In an apparatus aspect, a channel light measurement apparatus is provided. The channel light measurement apparatus includes a discrete photodetector array, and a variable integrate and hold circuit coupled to the discrete photodetector array wherein the variable integrate and hold circuit comprises adjustment capability allowing adjustment of a sampling factor comprising an integration time, a value of capacitance, an area of the discrete photodetector array, or combinations thereof.

In a system aspect, a multi-channel light measurement system is provided. The multi-channel light measurement system includes a light source operable to provide light emission over a primary wavelength range, light separator adapted to split the light emission over the primary wavelength range into a plurality of wavelength sub-ranges, an array of photodetectors, each adapted to receive light emissions over at least some of the plurality of wavelength sub-ranges and output a reference intensity signal for each of the photodetectors in the array, and a multi-channel measurement circuit comprising multiple channels with a channel corresponding to each of the plurality of wavelength sub-ranges, the multi-channel measurement circuit configured and operable to receive the reference intensity signals from the array of photodetectors, and adjust a sampling factor for at least some of the channels.

Still other aspects, features, and advantages of the present invention may be readily apparent from the following detailed description by illustrating a number of example embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention is to cover all modifications, equivalents, and alternatives falling within the scope of the invention.

DETAILED DESCRIPTION

As discussed above, in automated clinical analyzers, achieving precision and simplicity in the illumination of test samples is desirable. For systems that include light measurements taken at multiple wavelengths, the intensity of the light source may vary quite significantly over the multiple measured wavelength sub-ranges. Moreover, a responsiveness of the detection photodiode may also vary at a given wavelength sub-range. In particular, the measured intensity level may vary substantially over the range of wavelengths measured. For example, an intensity of a halogen light source may be much less at the relatively lower wavelengths of its output range. Additionally, a response of the photodiode may be much less at relatively lower wavelengths as compared to the upper wavelengths. As such, the light measurements taken may have intensity values, some of which have relatively high intensities and some with relatively low intensities over a measured wavelength range. The inability to provide approximately the same voltage output (near full scale conversion) at each wavelength may limit both the precision and range possible in prior systems.

A typical method to account for these intensity differences is to provide an operational amplifier at each photodiode output with different gains. For example, higher gains may be applied at the lower wavelengths and lower gains at the upper wavelengths. However, when the gain is increased to increase the intensity level output of a particular channel, the electrical noise for that channel is also amplified. Therefore, a signal-to-noise ratio may be decreased.

Accordingly, methods, systems, and apparatus that improve precision of measuring light emissions at multiple wavelengths are desired. This is especially true for those channels exhibiting relatively low intensities as compared to the other channels being sampled.

In view of the foregoing problems, embodiments of the present invention provide methods, systems, and apparatus adapted to illuminate and measure light at multiple wavelengths. In particular, multi-channel light measurement methods, systems, and apparatus are provided that enable measurement of a test sample contained in a test vessel with improved precision, especially when light intensities of a light source at multiple sampled wavelengths are different.

In a first aspect, a method receives light emissions over wavelength sub-ranges at an array of photodetectors wherein each photodetector receives light emissions over a discrete wavelength sub-range, providing a multi-channel measurement circuit comprising multiple channels with each channel corresponding to at least one photodetector, and adjusting sampling factors for at least some of the channels based on a measured reference light intensity of wavelength sub-ranges to arrive at channel reference values.

These and other aspects and features of the invention will be described with reference to FIGS. 1-7 herein.

Figure 1:
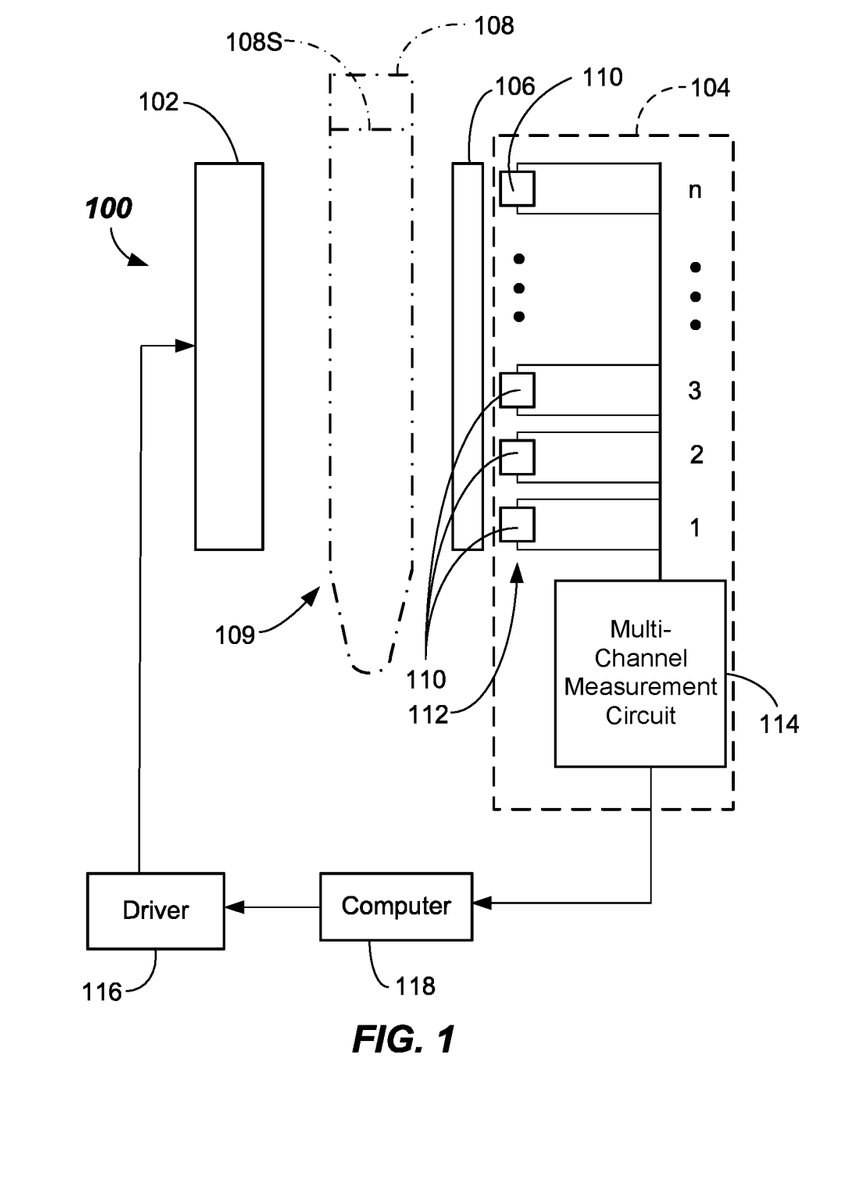
FIG. 1 illustrates a block diagram view of a multi-channel light measurement system according to embodiments.

In accordance with a first embodiment, as best shown in FIG. 1, a multi-channel light measurement system 100 is depicted. The multi-channel light measurement system 100 includes a light source 102 and a light measuring circuit 104. The light source 102 may be a halogen light source such as a quartz tungsten halogen light source, for example. Other types of white light sources may be used. The light source 102 may be driven by direct current continuously near its power rating in order to provide a stable output over the entire primary spectral emission range. The halogen light source 102 may have a primary emission wavelength range of between about 300 nm and about 1200 nm, for example. Light sources 102 having other ranges may be used. For this light source 102, the output light intensity may vary over an entire range in that the output intensity may be relatively small in the wavelength range from 340 nm to 450 nm as compared to the wavelength range from 500 nm to 900 nm. Thus, the output intensity at the lower wavelengths may be substantially less than the output intensity at the upper wavelengths. This difference is accommodated for by embodiments of the invention, while providing relatively high signal-to-noise ratio in the signal output as will be apparent from the following.

The light measurement system 100 may further include a light separator 106. The light separator 106 functions to separate the white light emission from the light source 102 into multiple wavelength sub-ranges. In particular, the light may be separated by the light separator 106 on the other side of a vessel 108 from the light source 102 into n channels of relatively narrow discrete wavelengths sub-ranges of about 10 nm wide. Other width ranges may be used. The separation into the n discrete wavelengths sub-ranges can be accomplished by any suitable device or method. For example, the light separator 106 may be an array of band-pass filters, a beam splitter and an array of band-pass filters, fiber optic channels and bandpass filters, or a diffraction grating, for example. Other types of light separators may be used.

The light travels through the vessel 108 containing the test sample 108S, and is directed through the separator 106, which may include a set of band-pass channel filters, one for each channel 1-n. The band-pass channel filters of the separator 106 may be manufactured from a borosilicate float glass material having thin films applied thereon such that each may have a specifically-designed region of transmittance, bounded by defined regions of spectral rejection. The filters may be optical band-pass filters, such as available from Newport Corporation of Irvine, Calif., for example. Other types of filters may be used. Light through each band-pass channel filter is directed onto an individual photodetector per channel, or optionally a discrete photodiode array 110 per channel. The photodetectors may be Si photodiodes. A model S9702 photodiode from Hamamatsu Corporation of Bridgewater, N.J. may be used. Other sizes and types of photodetectors may be used.

In the depicted embodiment, light from each channel 1-n is directed onto a discrete photodetector array 110 (e.g., a photodiode array) in an array of photodetectors 112. The number of discrete photodetectors in the discrete photodetector array 110 may include 2, 3, 4, 5, or more, for example. However, in some embodiments, a discrete array may not be used and only one photodetector per channel may be provided. The number of channels n may be greater than 6, greater than 8, greater than 10, greater than 12, or even 14 or greater in some embodiments. In some embodiments 14 channels and, thus, 14 discrete photodetector arrays 110 may be used. Other numbers of channels n may be used.

The light measurement system 100 is useful and operable to illuminate a test sample 108S that is contained in the vessel 108 (e.g., a cuvette or a sample flow-through passage). Any suitable configuration of vessel 108 adapted to contain a test sample 108S to be illuminated may be used. The test sample 108S provided in the light measurement system 100 may have been aspirated from a sample container held in a sample rack or at another location, for example. In some embodiments, one or more reagents from a reagent container(s) (not shown) may be added to form the test sample 108S contained in the vessel 108 and promote a reaction with an analyte, material, or constituent in the test sample 108S. Other materials and/or liquids (e.g., purified water) may be included in the test sample 108S, as well. However, it should be apparent that the light measurement system 100 may be used to illuminate test samples 108S that do not contain a reagent or other liquid, i.e., just the biological fluid sample.

In FIG. 1, the vessel 108 may include a slender channel having transparent side walls that extend along the length of the vessel 108 such that light may pass through the vessel 108 in a relatively unimpeded fashion. The vessel 108 may be made of a transparent material such as glass, or highly transparent acrylic plastic such as a polymethyl methacrylate plastic, for example. Other transparent materials may be used. During calibration of the light measurement system 100, the vessel 108 may be removed, and during sample testing, the vessel 108 with test sample 108S contained therein may be inserted into a space 109 in the multi-channel light measurement system 100. The vessel 108 may be provided in the space 109 located between the light source 102 and the light separator 106 in some embodiments.

Again referring to FIG. 1, the multi-channel light measurement system 100 may be included in a clinical analyzer or other suitable testing instrument at any suitable location. The multi-channel light measurement system 100 may include brackets adapted to rigidly mount the light source 102, light separator 106, and the array of photodetectors 112 in a fixed orientation relative to a frame (not shown) of the clinical analyzer or instrument. Mounted within the clinical analyzer or instrument may be the light measuring circuit 104. In the depicted embodiment, the light measuring circuit 104 includes a multi-channel measurement circuit 114 comprising multiple channels 1-n with a channel 1-n corresponding to each photodetector (or discrete photodetector array 110) in the array of photodetectors 112. Thus, it should be apparent that in some embodiments, only a single photodetector is used per channel 1-n.

In the depicted embodiment, the light measurement system 100 includes a discrete number of wavelength sub-ranges that span a wavelength range from about 340 nm to about 880 nm, for example. Other wavelength ranges may be used. The light source 102 is driven by a driver 116, and may be driven with constant DC current. A suitable computer 118 may be used to process data received from the multi-channel measurement circuit 114 and determine a degree of absorption, emission, fluorescence, chemiluminescence, or combinations thereof for each channel 1-n. The computer 118 may be any suitable computer having a processor or microprocessor, memory and interfaces for receiving reference and intensity signals from the various channels 1-n and carrying out the above calculations and/or determinations. Any suitable method for calculating or determining a degree of absorption, emission, fluorescence, chemiluminescence, or combinations thereof may be used. For example, values for each channel 1-n may be determined by using the reference values obtained during a calibration (startup) step together with measured values obtained for each channel 1-n during a test measurement (testing) step with the light measurement system 100.

Figure 2:
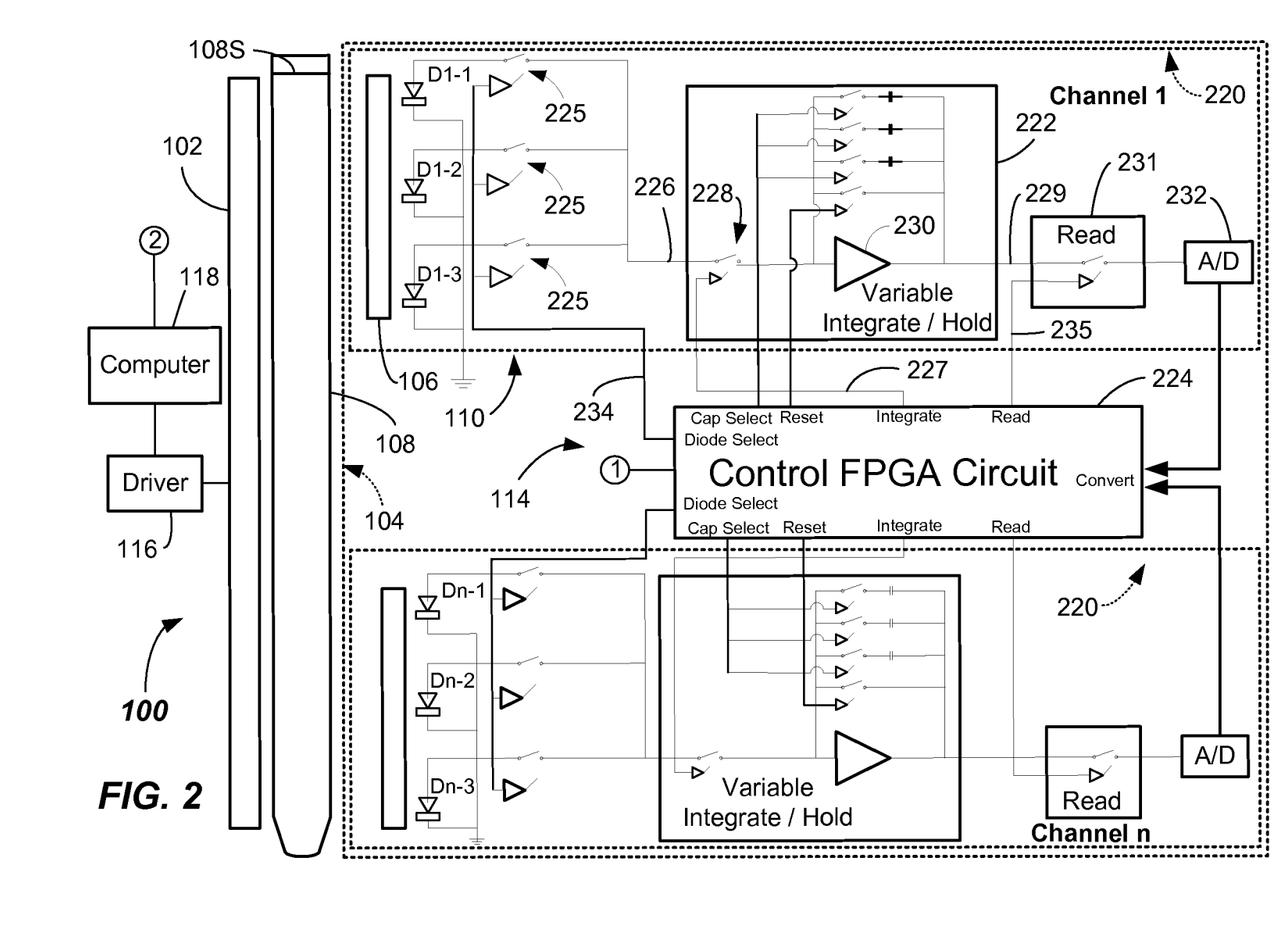
FIG. 2 illustrates a detailed block diagram view of a multi-channel light measurement system according to embodiments.

Now referring to FIG. 2, an embodiment of the light measurement system 100 including a multi-channel measurement circuit 114 is shown in more detail. Each channel 1-n includes a channel light measurement apparatus 220. Only two channels (1 and n) are shown, but any number of channels 1-n may be used, as discussed above. The channel light measurement apparatus 220 will be described with reference to channel 1. The channel light measurement apparatus 220 may include the same components and structure for each channel 1-n, although the values of some components (e.g., capacitor values) described may differ in some embodiments.

Each channel light measurement apparatus 220 includes a discrete photodetector array 110 and a variable integrate and hold circuit 222 electrically coupled to the discrete photodetector array 110. The variable integrate and hold circuit 222 comprises adjustment capability enabling adjustment of a sampling factor. The sampling factor may comprise an integration time, a value of capacitance, a receiving area of discrete photodetector array 110, or any combination thereof. Accordingly, the sampling factor may be adjusted for at least some of the channels 1-n based on a measured light intensity of at least some of the channels 1-n, i.e., for at least some of the plurality of wavelength sub-ranges. In some embodiments, the sampling factors are adjusted for all channels 1-n.

The discrete photodetector array 110 may comprise two or more photodiodes (e.g., D1-1, D1-2, D1-3, or more), which may be selectively engaged by the Diode Select function of a control field programmable gate array (FPGA) circuit 224 in line 234. The discrete photodetector array 110 comprising discrete photodiodes (e.g., D1-1, D1-2, D1-3, or more) may be a Model # S4111-35Q photodiode available from Hamamatsu Photonics K.K. of Hamamatsu City, Japan. Other suitable photodiodes may be used. The control FPGA circuit 224 may be a Spartan 6 available from Xilinx Inc., for example. Other types of control FPGA circuits 224 may be used. When engaged via activation of one or more of switches 225, a channel light intensity signal for channel 1 may be sent to the variable integrate and hold circuit 222 in intensity signal line 226 when the integrate switch 228 is activated (closed) by a signal from the control FPGA circuit 224 in integrate line 227. The variable integrate and hold circuit 222 integrates the signal input from intensity signal line 226 and passes an integrated signal from the integrator comprising amplifier 230 to read switch 231 in output signal line 229. The read switch 231 may allow the signal to pass through to the A/D converter 232 and to the control FPGA circuit 224 operating as a buffer for the computer 118, or be read through read line 235 based upon the position of the read switch 231. In the read condition, the control FPGA circuit 224 may read the integrated signal in output signal line 229 and determine whether it should have a sample factor adjusted for channel 1 based upon like readings taken for other channels 2-n during a calibration step. Once the sample factors are set for all channels 1-n, reference values may be sent through the A/D converter 232, buffered in the control FPGA circuit 224, and sent to computer 118 for storage in memory for use and comparison in later sample testing.

Figure 3:
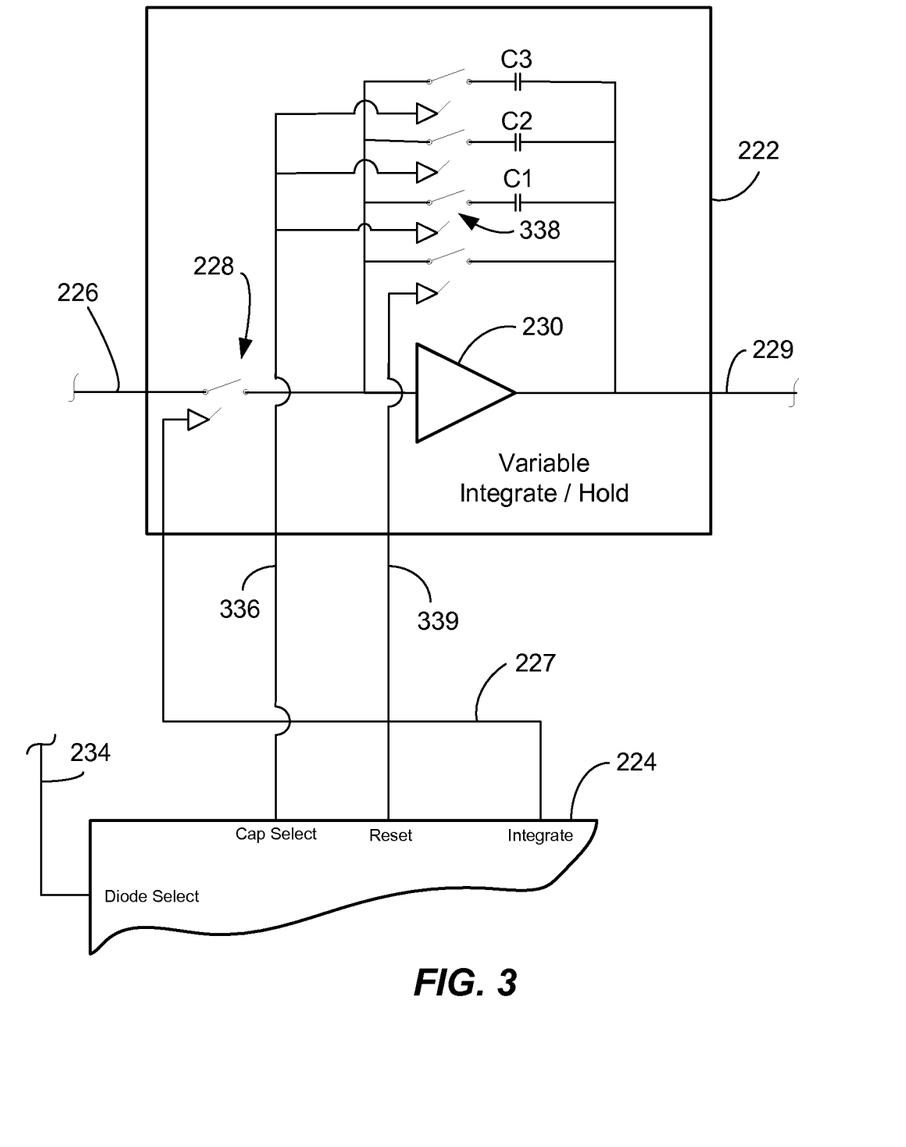
FIG. 3 illustrates a detailed block diagram view of a channel variable integrate and hold circuit according to embodiments.

Now referring to FIG. 3, an enlarged view of a variable integrate and hold circuit 222 is shown. The adjustable sampling factor of the variable integrate and hold circuit 222 may be provided by adjusting an integration time, a value of capacitance, an area of the discrete photodetector array 110, or combinations for at least some or all of the channels 1-n. For example, in a first example, a capacitor C1 may be selected by the Cap Select of the control FPGA circuit 224 via a signal in capacitor select line 336, closing switch 338 and effectively providing a first integrate value of the amplifier 230. In one example, a lowest capacitance value and thus a lowest integrate value may be selected initially for running a reference intensity level test for each channel 1-n so that the intensity variations per channel 1-n may be determined. Then the sample factor may be changed by changing a value for capacitance for each channel 1-n in this embodiment. Changing the capacitance value may be achieved by selecting C1, C2, C3, or combinations thereof. This may be used to provide an approximately equal output signal level in output signal line 229 to the A/D converter 232 for each channel 1-n. The selected values may be selected so that a signal level is at or near the top range of the A/D converter 232 (e.g., between about 80% and about 90% of full range) may be provided. Any value of C1, C2, C3, or combinations thereof may be selected so a wide range of capacitance values may be set. In some embodiments, the values of C1, C2, and C3 may be between about 10 pF and 60 pF, for example. Other capacitor values may be provided. The selected values may, and likely will, be different per each channel 1-n in order to approximately equilibrate the intensity output signal in output signal line 229 for each channel 1-n. In this embodiment, the integration time via activation of integrate switch 228 may be held constant for all channels 1-n. The capacitor values C1-C3 may be reset during subsequent recalibrations by sending a signal in reset line 339 to bleed off any charge on the selected capacitors.

In another embodiment, the integration time may be varied per channel 1-n. For example, a common value of capacitance (e.g., C1) may be selected via Cap Select of the control FPGA circuit 224 for all channels 1-n, and then the sample factor may be varied per channel 1-n by adjusting an integration time via signal in integrate line 227 to control a closed duration of switch 228 and vary an integration duration for each channel 1-n. The more time that is allotted for integration by the variable integrate and hold circuit 222, the more voltage that is provided for a given output signal at 229. Again, the read switch 231 may be activated by the control FPGA circuit 224 and the output values may be read and then the integration times may be adjusted per channel 1-n with the goal of approximately equilibrating signal outputs in output signal line 229 for each channel 1-n.

In another embodiment, the photodetector area may be adjusted per channel 1-n. For example, one, two, three, or more of the depicted individual diodes D1-1, D1-2, D1-3, or more of the discrete photodetector array 110 may be selected by the Diode Select of the control FPGA circuit 224 via a signal in diode select line 234 to switches 225. Accordingly, the sample factor may be varied per channel 1-n by adjusting the exposed photodetector area for each channel 1-n. The more sensor area that is allotted, i.e., the more photodetectors (e.g., photodiodes) selected, the more voltage that is provided at the output signal line 229. Again, the read switch 231 may be activated by the control FPGA circuit 224 and the output values may be read and then the number of selected photodetectors of the discrete photodetector array 110 may be adjusted per channel 1-n with the goal of approximately equilibrating signal outputs in output signal line 229 for each channel 1-n.

The Diode Select and Cap Select signals may be selected during setup (e.g., a calibration step) of the multi-channel light measurement system 100 and the values, once selected, are not changed during a later test sample measurement step. During recalibration and reset of the values during calibration, the Reset signal from the control FPGA circuit 224 in reset line 339 may be for a fixed predetermined time that has been proven empirically to set the integrator output to 0 volts for the timing used for measurement and is generally the same for each channel 1-n.

A recalibration of the light measurement system 100 may occur multiple times during the day, every day, or after every so many tests, for example. Other calibration intervals may be used. The "ON" time for the Integrate signals in integrate line 227 are selected during setup (calibration) and, as discussed above, each channel 1-n may have its own integration time. The integration time, once set during calibration, is then used for each test measurement of the test sample 108S.

In the depicted embodiment, the read output signal in read line 235 can be in a constant "ON" mode if a single A/D converter 232 is used to pass the signal directly to the computer 118 or to the FPGA circuit 224 as a buffer, as shown. In an optional embodiment, the read switch 231 may function as a multiplexer if a single A/D is used to read the outputs of multiple channels 1-n, and pass those signals to the FPGA 224 or computer 118 such as in a sequential fashion.

Although the system 100 allows the choice of three different selections for sample factor per channel 1-n, that is: selecting photodetector area from a discrete photodetector array, setting a capacitor value, or adjusting an integration time, any one of these could be used alone, or in any combination. For example, selecting photodetector area per channel may be used for gross corrections in amplitude of the signal output in output signal line 229 and a combination with integration time may be used for fine control with a goal to approximately equilibrate reference output signals in output signal line 229 for each channel 1-n. Capacitance may be held constant for all channels in this embodiment.

In another example, setting capacitance values may be used for gross corrections in amplitude of the signal output for each channel 1-n, and integration time may be used in combination for fine control to approximately equilibrate reference output signal per channel in the output signal line 229 for each channel 1-n. A maximum number of photodetectors of each discrete array of photodetectors 110 may be selected and held constant for all channels 1-n in this embodiment.

In another example, selecting photodetector area per channel 1-n may be used for gross corrections in amplitude of the signal output, and the capacitance value may be set in combination for fine control to approximately equilibrate the reference output signal per channel in output signal line 229 for all channels 1-n. Integration time may be held constant per each channel in this embodiment. In another option, all three may be used.

As yet another example of a setup (calibration) of the light measurement system 100, the light source 102 may be turned and allowed to stabilize. All photodiodes (e.g., three shown) in the discrete array 110 for each channel 1-n may be selected, and all three capacitors C1, C2, C3 for each channel 1-n may be selected to provide a maximum capacitance value for each channel 1-n. During calibration (or recalibration) an open light path is provided, i.e., no cuvette or sample is provided in the path.

The integration period may be selected via integrate signal 227 being set at a maximum time allowed for a measurement (e.g., about 500 µs). Each channel 1-n may be sampled, and the output voltage levels read in read line 235. If the voltage values for a given channel are at the saturation level, i.e., at a maximum value of the A/D converter 232, then the integration time may be lowered for that particular channel until the measurement is within a suitable range less than the full range value of the A/D converter 232 (e.g., about 80%-90% of full range), but not saturated. Other suitable percentage values may be used.

In general, there should also be a minimum time for integration, since an area of the vessel 108 (e.g., cuvette) should be sampled in operation to minimize any effects from defects that may be on the cuvette surface. If the integration time is too short, the Diode Select of the control FPGA circuit 224 may be used to select only two of the photodetectors (e.g., photodiodes) of the discrete photodetector array 110 in a given channel and measurements again taken in read line 235 on that channel after further adjustment of the integration time. If this fails, then only one of the photodetectors (e.g., photodiodes) of the discrete photodetector array 110 may be selected and the process may be repeated. It should be noted that the capacitor values C1-C3 may be initially selected (hardware installed) such that, in theory, the maximum capacitance selected should not saturate any channel 1-n based on a minimum selected integration time when only one photodetector (e.g., photodiodes) of the discrete photodetector array 110 is selected for any given light source 102 that is used in operation.

If the initial measurement for a given channel 1-n is too low with the maximum integration time, and all three of the capacitors C1-C3 are selected, the capacitor value may be reduced and the integration process may be repeated. In particular, it should be verified that the output signal level in output signal line 229 with the smallest capacitance C1 selected, with three photodetectors (e.g., photodiodes) of the discrete photodetector array 110 selected, and with a maximum integration time selected should be within a predetermined range of full scale of the A/D converter 232. For example, the predetermined range of full scale of the A/D converter 232 may be between about 80% and about 90% of full scale. Other ranges may be used.

This calibration method may be accomplished at instrument startup, installation of a new light source, when a service flag shows reduced light intensity, or at other intervals as discussed above.

Figure 4:
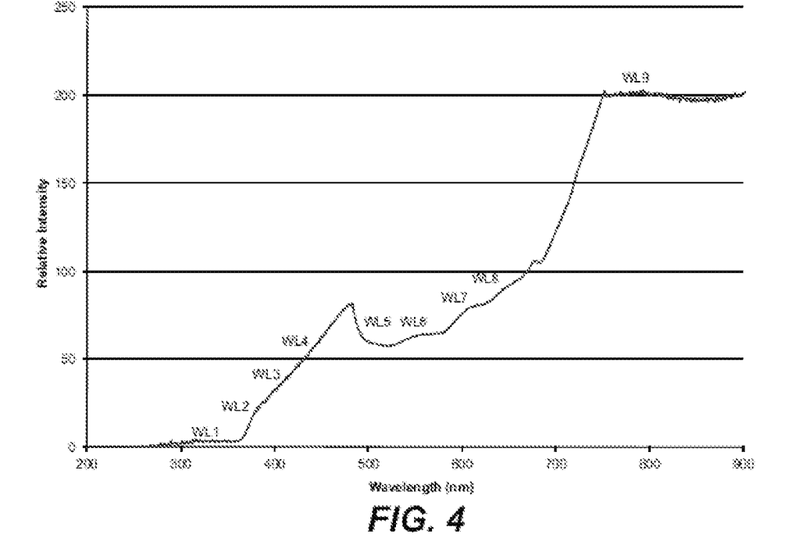
FIG. 4 is a plot of light intensity per channel for a prior art multi-channel light measurement system.

FIG. 4 illustrates a light intensity output per channel for a nine channel system without any gain adjustment or other amplitude adjustment and illustrates the dissimilar voltage output levels for each channel WL1-WL9 across the overall wavelength range, and especially illustrates the low voltage output levels at the lower wavelength sub-ranges (e.g., WL1-WL3).

Figure 5:
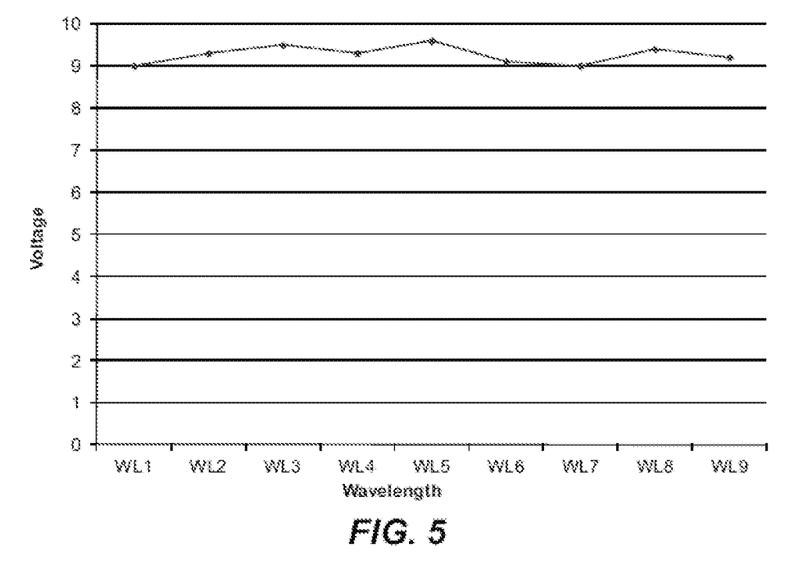
FIG. 5 is a plot of light intensity per channel for a multi-channel light measurement system according to embodiments.

FIG. 5 illustrates light intensity that has been equilibrated according to embodiments of the present invention. In particular, the output level has been adjusted per channel WL1-WL9 by adjusting the aforementioned sampling factors per channel 1-n for at least some, and preferably all, of the channels 1-n. In particular, the equilibration comprises setting one or more of the sampling factors (e.g., integration time, capacitance level of the variable integrate and hold circuit 222, or receiving area of the discrete photodetector array 110) for at least some, and, in some embodiments, all of the channels WL1-WL9 to achieve output voltages that vary by no more than a predetermined amount. The predetermined difference may be no more than about +/−10% from an average thereof, or no more than even about +/−15% from an average thereof. The sampling factors may also be set so that between about 80% and about 90% of the full scale of the A/D converter for each channel 1-n is achieved.

Figure 6:
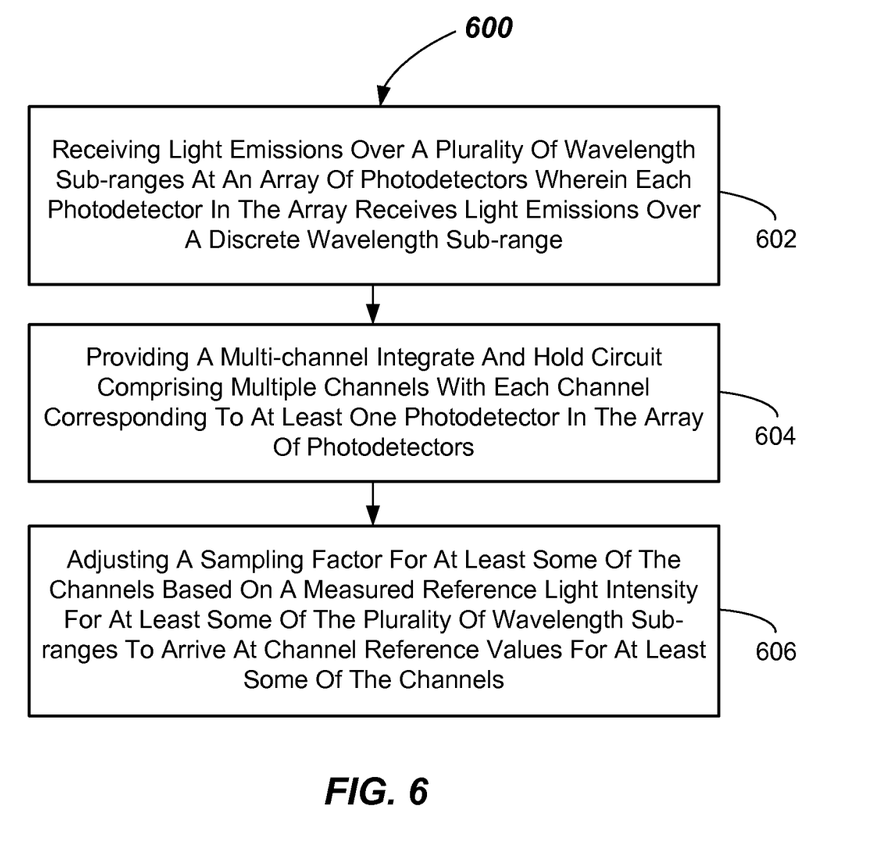
FIG. 6 is a flowchart illustrating a multi-channel light measurement method according to embodiments.

A multi-channel light measurement method 600 according to embodiments of the invention will now be explained with reference to FIG. 6 herein. The method 600 includes receiving in 602 light emissions over a plurality of wavelength sub-ranges at an array of photodetectors (e.g., 112), wherein each photodetector in the array receives light emissions over a discrete wavelength sub-range, providing, in 604, a multi-channel measurement circuit (e.g., 114) comprising multiple channels 1-n with each channel 1-n corresponding to at least one photodetector in the array of photodetectors (e.g., 112), and adjusting, in 606, a sampling factor (e.g., integration time, capacitance level of the variable integrate and hold circuit 222, or receiving area of the discrete photodetector array 110) for at least some of the channels 1-n based on a measured reference light intensity for at least some of the plurality of wavelength sub-ranges to arrive at channel reference values for at least some (and, in most embodiments, all) of the channels 1-n.

Figure 7:
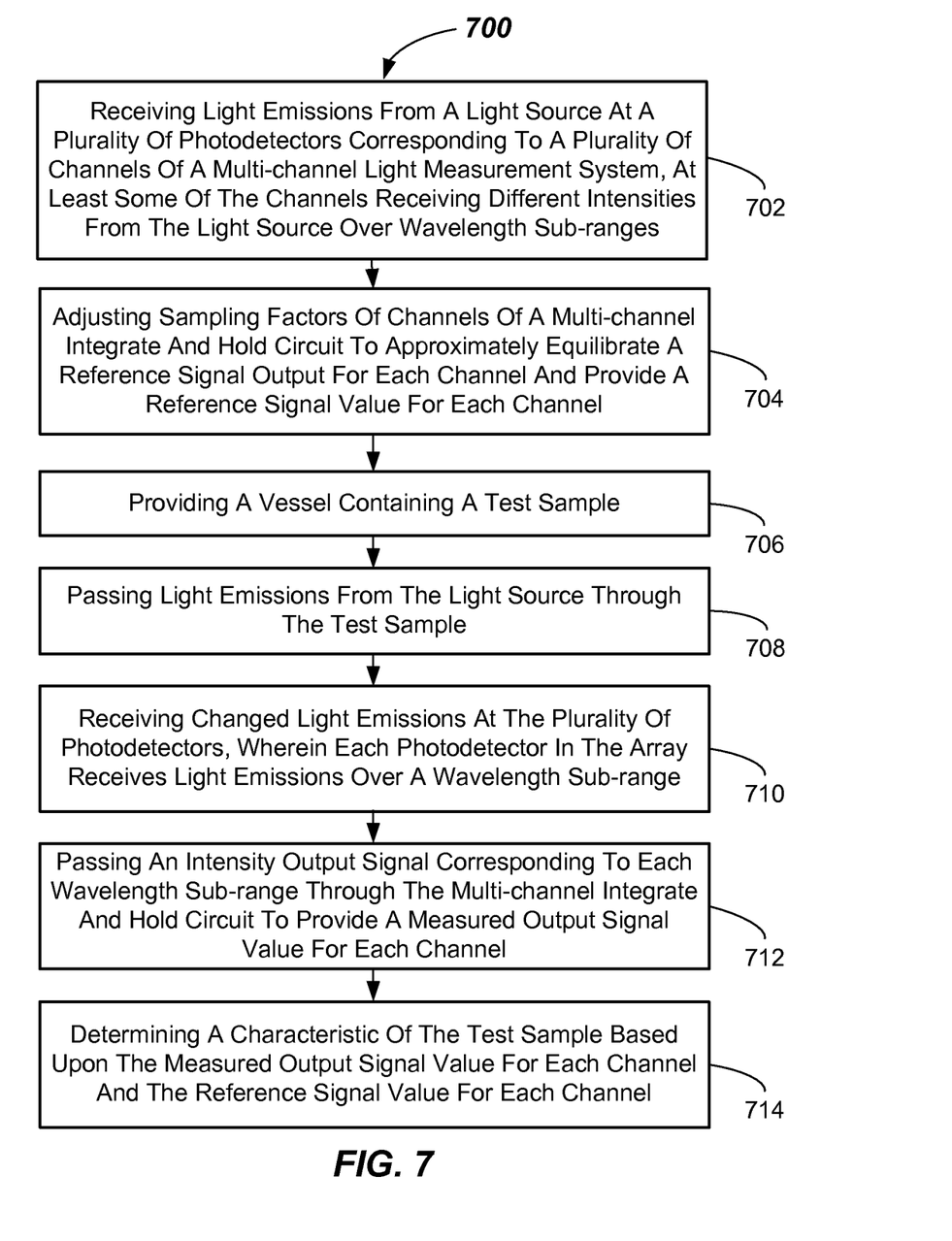
FIG. 7 is a flowchart illustrating a multi-channel light measurement method according to embodiments.

A multi-channel light measurement method 700 according to embodiments of the invention will now be explained with reference to FIG. 7 herein. The method 700 includes receiving in 702 light emissions from a light source (e.g., 102) at a plurality of photodetectors (e.g. 112) corresponding to a plurality of channels 1-n of a multi-channel light measurement system (e.g., 100), at least some of the channels 1-n receiving different intensities from the light source over wavelength sub-ranges (e.g., as shown in FIG. 4), adjusting sampling factors (e.g., integration time, capacitance level of the variable integrate and hold circuit 222, or receiving area of the discrete photodetector array 110) of channels of a multi-channel measurement circuit (e.g., 114) to approximately equilibrate a reference signal output (e.g., at output signal line 229) for each channel 1-n and provide a reference signal value for each channel 1-n in 704. The method 700 further includes in 706 providing a vessel (e.g., 108) containing a test sample (e.g., 108S), passing light emissions from the light source (e.g., 102) through the test sample in 708, receiving changed light emissions at the plurality of photodetectors (e.g., array 112), wherein each photodetector receives light emissions over a wavelength sub-range in 710, passing an intensity output signal corresponding to each wavelength sub-range through the multi-channel measurement circuit (e.g., 114) to provide a measured output signal value for each channel 1-n in 712, and determining a characteristic of the test sample based upon the measured output signal value for each channel 1-n and the reference signal value for each channel 1-n in 714. The characteristic may be any of the above-listed.

While the invention is susceptible to various modifications and alternative forms, specific system and apparatus embodiments and methods thereof have been shown by way of example in the drawings and are described in detail herein. It should be understood, however, that it is not intended to limit the invention to the particular systems, apparatus, or methods disclosed but, to the contrary, the intention is to cover all modifications, equivalents, and alternatives falling within the scope of the invention.

What is claimed is:

1. A channel light measurement apparatus, comprising:
   a plurality of discrete photodetector arrays, each one of the plurality of discrete photodetector arrays configured to detect light from a respective channel of a wavelength sub-range; and
   a plurality of variable integrate and hold circuits coupled respectively to the plurality of discrete photodetector arrays wherein each variable integrate and hold circuit comprises adjustment capability allowing adjustment of a sampling factor comprising an integration time, a value of capacitance, an area of the discrete photodetector array, or combinations thereof, each variable integrate and hold circuit comprising an amplifier and selectable capacitance coupled in parallel with the amplifier.

2. The channel light measurement apparatus of claim 1, wherein the adjustment capability of the value of capacitance comprises selecting at least one from a plurality of selectable capacitors of the variable integrate and hold circuit.

3. The channel light measurement apparatus of claim 1, wherein the adjustment of the integration time comprises adjusting the integration time based upon a read output signal from the variable integrate and hold circuit.

4. A multi-channel light measurement system, comprising:
- a light source operable to provide light emission over a primary wavelength range;
- a light separator adapted to split the light emission over the primary wavelength range into a plurality of wavelength sub-ranges;
- an array of photodetectors, each adapted to receive light emissions over at least some of the plurality of wavelength sub-ranges and output a reference intensity signal for each of the photodetectors in the array; and
- a multi-channel measurement circuit comprising multiple channels with a channel corresponding to each of the plurality of wavelength sub-ranges and further comprising a plurality of variable integrate and hold circuits each for a respective channel, each of the variable integrate and hold circuits comprising an amplifier and selectable capacitance coupled in parallel with the amplifier, the multi-channel measurement circuit configured and operable to:
  - receive the reference intensity signals from the array of photodetectors, and
  - adjust a respective sampling factor for each of the channels.

5. The multi-channel light measurement system of claim 4, wherein the sampling factor comprises setting a value of capacitance for at least some of the channels of the multi-channel integrate and hold circuit.

6. The multi-channel light measurement system of claim 4, wherein the sampling factor comprises adjustment of an integration time for at least some of the channels of the multi-channel measurement circuit.

7. The multi-channel light measurement system of claim 4, wherein the sampling factor comprises selection of an area of a discrete photodetector array for at least some of the channels.

* * * * *